United States Patent [19]

Quinlan

[11] Patent Number: 5,658,768
[45] Date of Patent: Aug. 19, 1997

[54] PROCESS FOR PRODUCTION OF HUMAN MILK FAT REPLACERS BY ENZYMATIC CONVERSION OF TRIGLYCERIDES

[75] Inventor: Paul Thomas Quinlan, Kempston, Great Britain

[73] Assignee: Loders Croklaan B.V., Wormerveer, Netherlands

[21] Appl. No.: 545,761

[22] PCT Filed: Apr. 22, 1994

[86] PCT No.: PCT/EP94/01304

§ 371 Date: Nov. 7, 1995

§ 102(e) Date: Nov. 7, 1995

[87] PCT Pub. No.: WO94/26854

PCT Pub. Date: Nov. 24, 1994

[30] Foreign Application Priority Data

May 13, 1993 [GB] United Kingdom ............... 93303713

[51] Int. Cl.$^6$ ................ C12P 7/64; C12P 7/62; A23D 7/00
[52] U.S. Cl. ............. 435/134; 435/135; 426/33; 426/601
[58] Field of Search ................... 435/134, 135; 426/33, 601

[56] References Cited

U.S. PATENT DOCUMENTS

| 4,275,081 | 6/1981 | Coleman et al. | 426/33 |
| 4,876,107 | 10/1989 | King et al. | 426/601 |
| 5,061,498 | 10/1991 | Matsuzaki et al. | 426/33 |
| 5,286,633 | 2/1994 | Moore | 435/134 |

FOREIGN PATENT DOCUMENTS

| 209 327 | 1/1987 | European Pat. Off. . |
| 417 823 | 3/1991 | European Pat. Off. . |
| 496 456 | 7/1992 | European Pat. Off. . |
| 0519542A1 | 12/1992 | European Pat. Off. . |

OTHER PUBLICATIONS

Japanese Abstract of Publication No. J62–000287, Derwent Info. 1995.

*Primary Examiner*—John W. Rollins
*Assistant Examiner*—Christopher R. Tate
*Attorney, Agent, or Firm*—Cushman Darby & Cushman IP Group Pillsbury Madison & Sutro LLP

[57] ABSTRACT

Triglycerides with more than 40 wt % saturated fatty acids in the 2-position contain considerable amounts of trisaturated triglycerides; these trisaturated triglycerides are removed (reduced) by performing an enzymic conversion with a source providing unsaturated $C_{18}$ to $C_{22}$ residues, using a 1,3-specific enzyme.

7 Claims, No Drawings

PROCESS FOR PRODUCTION OF HUMAN MILK FAT REPLACERS BY ENZYMATIC CONVERSION OF TRIGLYCERIDES

This application claims benefit of international application PCT/EP94/01304, filed Apr. 22, 1994 published as WO94/26854, Nov. 24, 1994.

BACKGROUND OF THE INVENTION

The enzymic preparation of fats that can be used as human milk fat replacers, in which fats more than 40 wt. % of the total amount of saturated fatty acids present are in the 2-position, is the subject of our earlier European patent 0209327 (Application N° 86305325.2) and European patent application 91300496.6.

According to these processes, fats (A) high in trisaturated triglycerides (=$S_3$, wherein S is preferably palmitic) are converted with a source (B) that provides oleic acid moieties. Sources of B are, e.g., free fatty acid mixtures rich in oleic acid or triglycerides with a high oleic acid content in the 1,3-positions, e.g. high-oleic sunflower oil.

The conversion is carried out in the presence of a 1,3-specific enzyme. The product of this enzymic conversion containing residual amounts of non-converted $S_3$, partial conversion products, such as SSO, and the desired conversion products (OSO), is subjected to a fractionation process in which a product rich in OSO is obtained while a product rich in SSO is removed and recirculated to the conversion zone. Spent oleic acid sources (B) are removed in a strip zone and can be used again in the process, if and when appropriate.

Human milk replacement fats can only contain very limited amounts of trisaturated triglycerides ($S_3$, where S=saturated fatty acid with at least 16 C-atoms). When the amount of $S_3$ is too high, the fat becomes too hard, and simultaneously absorption of the fat by infants is affected adversely.

However, the products obtained in the enzymic conversion zone normally still contain amounts of 7 or more wt. % of $S_3$, which is above the level, generally regarded as acceptable (about 4 wt %). Only when these products were subjected to solvent fractionation could these levels be decreased to the desired level. However, wet fractionation requires high investments in equipment, time and energy and is therefore less attractive from a commercial point of view.

SUMMARY OF INVENTION

We have now found a new process by which the desired fats of maximum levels of 3 wt. % of $S_3$ are obtained and in which fractionation can be avoided.

Accordingly, our invention is concerned with a process for the preparation of triglyceride compositions, in which more than 40 wt. % of the total amount of saturated fatty acids present are in the 2-position, by enzymic interesterification of triglycerides high in trisaturates (=A) with a source (B) providing unsaturated fatty acid moieties ($C_{18}$ or more), which process is characterized by the performance of an enzymic removal, using a 1,3-specific enzyme, of trisaturated triglycerides (=$S_3$, S=$C_{16}$ or higher), in particular trisaturated triglycerides high in $P_3$ and/or $St_3$ (P=palmitic, St=stearic) or a combination thereof (PSt P. etc.) from a product high in triglycerides rich in 2-saturated fatty acids from the USU and/or SSU type (U=unsaturated fatty acids $C_{18}$ or more; S=saturated fatty acids $C_{16}$ or more) by contacting the product rich in USU and/or SSU with an oil blend high in triglycerides with acids other than palmitic and/or stearic acid in the 1,3-positions, but not being a triglyceride composition with more than 40 wt % of the fatty acids in the 2-position being saturated fatty acids with 16 or more C-atoms.

Preferably, blends are used which are rich in triglycerides having a high level of unsaturated fatty acids, such as oleic or linoleic acid or short chain saturated fatty acids, such as $C_{8:0}$; $C_{10:0}$ or $C_{12:0}$ in at least the 1,3-positions.

A preferred process is a multi-step process comprising the steps of:

1) converting triglycerides A enzymatically with a 1,3-specific enzyme and the unsaturated acid source B in a first enzymic conversion zone;

2) removing the spent unsaturated acid source B from the crude product of 1);

3) optionally subjecting the remaining part of 2) to an enzymic removal of diglycerides;

4) converting the remaining part of 2) and/or the product of 3) in a second enzymic conversion zone with a fresh source providing unsaturated acid moieties (B) in the presence of a 1,3-specific enzyme;

5) removing the spent unsaturated acid source B from the crude product of 4);

6) optionally recirculating the spent unsaturated acid source (B) from 5) to step 1);

7) decreasing the level of trisaturates ($S_3$, S=$S_{16}$ or higher) in the remaining part of 5) by a further enzymic treatment, using a 1,3-specific enzyme with an oil blend high in triglycerides with acids other than palmitic and/or stearic acid in the 1,3-positions, but not being a triglyceride composition with more than 40 wt % of the fatty acids in the 2-position being saturated fatty acids with 16 or more C-atoms.

DETAILED DESCRIPTION OF INVENTION

It is surprising to find in this case that a third enzymic conversion can replace the fractionation procedure, as the levels of $S_3$ after two previous enzymic conversions were still too high. In an alternative embodiment of the process the second enzyme conversion (steps 4 and 5 above) can be omitted, proceeding directly to step 7 by employing a sufficiently high ratio of acid to oil in step (1).

The above-mentioned process is in particular applicable to systems in which a fatty acid mixture high in oleic acid is used as source (B) providing oleic acid moieties.

Fats A, which can be used as fats high in trisaturates $S_3$ (S=palmitic and/or stearic), are in particular the top fractions of palm oil fractionation. These fats preferably contain more than 60 wt. % of $S_3$ (S=palmitic and/or stearic), while more than 20 wt. % of SSU (U=unsaturated) can also be present.

The best results are obtained when weight ratios of trisaturated fat A: unsaturated acid source B of 1:2–2:1 are applied in the first and/or the second enzymic conversion zones of steps 1) and/or 4).

The other process conditions in these enzymic zones can be chosen within the process conditions as disclosed in, e.g., GB 1,577,933, European patent 0209327 (86305325.2) and European patent application 91300496.6. In particular, water contents, water activity, solvent, selection of 1,3-specific enzyme, catalyst-supporting materials are mentioned in these documents.

As any enzymic conversion inevitably also leads to the formation of some diglyceride, it is very useful to subject the crude triglyceride products of the enzymic conversion(s) to a treatment with a catalyst specific for the conversion of diglycerides into glycerol. Very useful AMANO G-catalyst (Lipase G), a diglyceride-specific lipase, which is conventionally used for this purpose.

In step 7), the level of $S_3$ is decreased by enzymic conversion, using the oil blend which is high in triglycerides with acids other than palmitic and/or stearic acid in the 1,3-positions. It is very suitable to use for this purpose: medium chain triglycerides (i.e. MCT-oils, based on $C_8$–$C_{14}$ fatty acids), coconut oil, palm kernel, soybean oil, palm oil, rapeseed oil, high-oleic sunflower oil, olive oil, fish oil, fungal, algal or other lipid sources rich in long chain polyunsaturated fatty acids, such as $C_{20:4\ w\ 6}$ or $C_{22:6\ w\ 3}$, and butterfat, or mixtures thereof.

As well as being suitable for applications in infant formulas and infant foods as human milk fat replacers, fats derived from the above process are readily digestible and may also be applied in other foods, for example in confectionery, spreads, creams, bakery products, cooking oils and health foods, and as a component in clinical products.

Our invention will be further explained by the following non-limiting Example(s).

EXAMPLE I

Palm stearine was reacted with high oleic sunflower acids (1:1 by weight) by passing the mixture through a column packed with SP-392. The product of this reaction was distilled to remove fatty acids and treated with Lipase G to reduce the diglyceride level. The residual $S_3$ level in this product was 7.6%. This product was mixed with high oleic sunflower oil (1:1 by weight) and interesterified using SP-392 as catalyst. The silver phase HPLC analysis of the fat blend before and after interesterification is shown below:

| wt % | SSS | SOS | SSO | SLnS | SOO | OSO | OSln | OOO | >3DB |
|---|---|---|---|---|---|---|---|---|---|
| Physical Blend | 3.8 | 1.6 | 12.9 | — | 12.6 | 11.6 | 8.4 | 41 | 5.8 |
| After int$^n$ | 2.4 | 4.2 | 12.7 | 0.7 | 20.9 | 15.2 | 4.9 | 3.9 | 33.7 |

$S = \geq C_{16:0}$, $O$ = oleic, ln = linoleic, >3DB = >3 double bonds/triglyceride The fatty acid composition of this blend (unaffected by interesterification) was:

| Fatty acids | 12:0 | 14:0 | 16:0 | 18:0 | 18:1 | 18:2 | 18:3 |
|---|---|---|---|---|---|---|---|
| wt % | 0.2 | 0.6 | 22.6 | 3.8 | 63.5 | 7.7 | 0.1 |

Interesterification of the physical blend reduced the $S_3$ level by nearly 40%.

EXAMPLE II

Palm stearine was mixed with fatty acids (normal and high oleic sunflower plus canola acids) in a weight ratio of 1:0.75, the feed partially saturated with water and passed through a column packed with immobilised lipase (mucor miehei on duolite) (Noyo; code SP-392). The product of Step 1 was collected and the fatty acids removed by distillation (Step 2). Treatment of the oil fraction with lipase G (diglyceride-specific lipase; Amano Pharmaceutical Co) was used to reduce diglyceride levels (Step 3). Fresh acids were added to the resultant triglycerides in the same ratio as before, and passed through a second enzyme column (Step 4). The fatty acids stripping and lipase G steps were repeated (steps 5 and 6). The resultant triglyceride (50 parts) was mixed with liquid vegetable oils (30 parts) and coconut oil (20 parts) and passed through a third enzyme column containing SP-392 catalyst step 7). The final oil blend was refined. Step 7 reduced the SSS level from 10% to 2.7% in the refined oil.

Results

1. Product of Steps 4–6

1.1 Fatty acid composition

|  | $C_{16:0}$ | $C_{18:0}$ | $C_{18:1}$ | $C_{18:2}$ | $C_{18:3}$ |
|---|---|---|---|---|---|
| Total | 48.3 | 2.4 | 35 | 13.3 | 1.0 |
| 2-position | 91.9 | 0.4 | 6 | 1.4 | 0.4 |

1.2 Silver Phase HPLC

| SSS | SSU | USU | SUS | SUU | UUU |
|---|---|---|---|---|---|
| 10 | 40.4 | 42.3 | 0.8 | 3.2 | 3.4 |

2. Product of Step 7

1.1 Fatty Acid composition

|  | $C_{8:0-14:0}$ | $C_{16:0}$ | $C_{18:0}$ | $C_{18:1}$ | $C_{18:2}$ | $C_{18:3}$ |
|---|---|---|---|---|---|---|
| Total | 18 | 25 | 3.0 | 35.4 | 16.0 | 2.0 |
| 2-position | 15.7 | 42.8 | 0.2 | 16.5 | 16.0 | 2.8 |

(57% of total palmitate in 2-position)

$S_3$ level reduced to 2.7% ($s=C_{16:0}+C_{18:0}$)

EXAMPLE III

Palm stearine (1 part) was mixed with unsaturated fatty acids (2 parts) derived from vegetable sources, partially wetted and reacted by passing through a column packed with SP-392 lipase (step 1). The product of this reaction was distilled to remove fatty acids (step 2) and treated with lipase G to reduce the diglyceride level (step 3). This product (50 parts) was mixed with 20 parts coconut oil and 30 parts mixed vegetable oils (sunflower, high oleic sunflower, canola, soybean) and reacted by passing through a second enzyme column (step 4). The final product was collected and fully refined. The $S_3$ level after step 3 was 11.8%, and was reduced to 2.5% after step 4.

1. Product of Step 3

1.1 Fatty acid composition

|  | $C_{16:0}$ | $C_{18:0}$ | $C_{18:1}$ | $C_{18:2}$ | $C_{18:3}$ |
|---|---|---|---|---|---|
| Total | 51.1 | 2.3 | 35 | 10.5 | 1.1 |
| 2-position | 95.4 | 0.2 | 4.0 | 0.4 | 0.4 |

1.2 Silver Phase HPLC

| SSS | SSU | USU | SUS | SUU | UUU |
|---|---|---|---|---|---|
| 11.8 | 43.8 | 40.4 | 0.4 | 1.8 | 1.9 |

2.1 Fatty Acid analysis

|  | $C_{8:0-14:0}$ | $C_{16:0}$ | $C_{18:0}$ | $C_{18:1}$ | $C_{18:2}$ | $C_{18:3}$ |
|---|---|---|---|---|---|---|
| FAME | 18 | 25 | 3.0 | 35.2 | 17.0 | 1.6 |
| 2-position | 18.7 | 43 | 0.2 | 17.3 | 19.0 | 1.8 |

(57% of total palmitate in 2-position)
$S_3$ level reduced to 2.4% ($s=C_{16:0}+C_{18:0}$)

I claim:

1. A process for the preparation of triglyceride compositions, in which more than 40 wt. % of the total amount of saturated fatty acids present are in the 2-position, comprising (1) converting by enzymic interesterification, using a 1, 3-specific enzyme, triglycerides high in trisaturates A with an unsaturated fatty acid source B with 18 to 22 C-atoms to obtain a product mixture of 1,3-diunsaturated 2-saturated (USU) triglycerides, 1,2-disaturated 3-unsaturated (SSU) triglycerides, and trisaturated ($S_3$) triglycerides, and (2) decreasing the level of $S_3$ by enzymic removal, using a 1,3-specific enzyme, from a product high in triglycerides, rich in 2-saturated fatty acids selected from USU and SSU triglycerides by contacting the product mixture with an oil blend consisting essentially of triglycerides with saturated acid in the 1,3-positions, less than 40 wt. % of the fatty acids in the 2-position of said oil blend triglycerides being saturated fatty acids with 16 to 22 atoms.

2. A process for the preparation of triglyceride compositions, in which more than 40 wt. % of the total mount of saturated fatty acids present are in the 2-position, by enzymic interesterification of triglycerides A with unsaturated acid source B comprising the steps of:

1) converting triglyceride A high in trisaturates enzymatically with a 1,3-specific enzyme and the unsaturated acid source B in a first enzymic conversion zone;

2) removing spent unsaturated acid source B from crude product obtained in step 1);

3) optionally subjecting any remaining part of the crude product in step 2) to an enzymic removal of diglyceride;

4) converting the remaining part of the crude product of step 2) or product of step 3) in a second enzymic conversion zone with a fresh source of unsaturated acid source B in the presence of a 1,3-specific enzyme;

5) removing spent unsaturated acid source B from crude product of step 4);

6) optionally recirculating the spent unsaturated acid source B from step 5) to step 1);

7) decreasing the level of trisaturates in any remaining product of step 5) by further enzymic treatment, using a 1,3-specific enzyme by contacting the product of step 5) with an oil blend consisting essentially of triglycerides with saturated acid in the 1,3-positions, less than 40 wt. % of the fatty acids in the 2-position of said oil blend triglycerides being saturated fatty acids with 16 to 22 C-atoms.

3. A processing according to claim 1 or 2, wherein a fatty acid mixture high in oleic acid is used as the saturated acid source B.

4. A process according to claim 2, wherein weight ratios of trisaturated fat A: unsaturated acid source B of 1:2–2:1 are used in the first, first and second or second enzymic conversion zones of step 1), steps 1) and 4) or step 4).

5. A process according to claim 2, wherein in step 3) an enzyme specific for hydrolysis of diglycerides into glycerol is used.

6. A process according to claim 1 or 2, wherein the oil blend is selected from the group consisting of medium chain triglycerides based on $C_8$–$C_{14}$ fatty acids, coconut oil, palm kernel oil, soybean oil, olive oil, high-oleic sunflower oil, fish oil, rapeseed oil, palm oil, butterfat, and fraction thereof.

7. A process according to claim 1 or 2, wherein triglycerides A comprises a mixture rich in palmitic acid with more than 60 wt. % being palmitic, palmitic and stearic or stearic ($S_3$) and more than 20 wt. % being palmitic, palmitic and stearic or stearic and an unsaturated acid (SSU).

* * * * *